(12) United States Patent
Leon-Rovira et al.

(10) Patent No.: US 11,039,756 B2
(45) Date of Patent: Jun. 22, 2021

(54) FUNCTIONAL DISPOSABLE SHEATH

(71) Applicant: ONKO SOLUTIONS LLC, Austin, TX (US)

(72) Inventors: Noel Leon-Rovira, Monterrey (MX); Jesús-Manuel Seáñez-De-Villa, Monterrey (MX); Ulisses-Alberto Heredia-Rivera, Tamaulipas (MX); Yeimi-Guadalupe Arreola-Bucio, Estado de Mexico (MX); Luis Santamaria-Grarcia, Acayucan Veracruz (MX)

(73) Assignee: ONKO SOLUTIONS LLC, Austin, TX (US)

( * ) Notice: Subject to any disclaimer, the term of this patent is extended or adjusted under 35 U.S.C. 154(b) by 384 days.

(21) Appl. No.: 15/951,730

(22) Filed: Apr. 12, 2018

(65) Prior Publication Data
US 2018/0368725 A1 Dec. 27, 2018

Related U.S. Application Data

(60) Provisional application No. 62/484,442, filed on Apr. 12, 2017.

(51) Int. Cl.
*A61B 5/053* (2021.01)
*A61B 5/1459* (2006.01)
*A61B 5/00* (2006.01)

(52) U.S. Cl.
CPC ............ *A61B 5/053* (2013.01); *A61B 5/1459* (2013.01); *A61B 5/4331* (2013.01); *A61B 2562/0215* (2017.08); *A61B 2562/06* (2013.01); *A61B 2562/227* (2013.01); *A61B 2562/247* (2013.01)

(58) Field of Classification Search
CPC ..... A61B 5/053; A61B 5/1459; A61B 5/4331; A61B 2562/247; A61B 2562/0215; A61B 2562/06; A61B 2562/227
USPC .......................................... 600/373
See application file for complete search history.

(56) References Cited

U.S. PATENT DOCUMENTS

| | | | |
|---|---|---|---|
| 4,832,036 A * | 5/1989 | Cartmell | A61B 5/04087 600/396 |
| 5,855,551 A * | 1/1999 | Sklandnev | A61B 5/0059 600/310 |
| 6,723,049 B2 | 4/2004 | Sklandnev et al. | |
| 9,265,426 B2 * | 2/2016 | Zuluage | A61B 5/0088 |
| 9,289,172 B2 | 3/2016 | Rovira | |
| 2014/0357956 A1 * | 12/2014 | Salahieh | A61B 1/00082 600/160 |

FOREIGN PATENT DOCUMENTS

EP 0 865 761 9/1998

* cited by examiner

*Primary Examiner* — Linda C. Dvorak
*Assistant Examiner* — Nils A Potter
(74) *Attorney, Agent, or Firm* — Nixon & Vanderhye (57) ABSTRACT

An active sheath for a recognition probe of a handheld cancer screening device, in which the conductors and circuits are applied on the surface of the sheath such as in the form of a flexible circuit made of a biocompatible material and a flexible conductor or a conductive ink in the surface of the disposable cover's tip without the need to embed the electrodes or other components inside the plastic cover.

8 Claims, 8 Drawing Sheets

FUNCTIONAL DISPOSABLE SHEATH

BACKGROUND OF THE INVENTION

A. Field of the Invention

The present invention is related to handheld cancer screening devices having a recognition probe, which perform both optical and electrical measurements on the surface of the tissue and makes a diagnosis of the normal and pathological cells of the tissue, and more particularly to a functional disposable sheath for such portable cancer screening device.

B. Description of the Related Art

According to the World Health Organization (WHO), cervical cancer is the fourth most common cancer among women. Out of the 270,000 deaths from cervical cancer each year, more than 85% happen in developing countries.

The problem surrounding cervical cancer detection in developing countries is the lack of accurate cervical screening to detect pre-cancerous lesions at an early stage. This means cervical cancer is not detected until its advanced stages when symptoms appear and when treatment is more complicated, resulting in an elevated death toll.

With the objective of providing accurate and accessible cervical screening options for women in developing countries, several biomedical devices that make use of optical and electrical measurements have appeared. These techniques have been widely used for the detection of diseases and bacterial agents in the field of medicine, based in reflective spectroscopy (optical measurements) and measurements of bioimpedance in the tissue (electrical measurements.). For example, U.S. Pat. No. 6,723,049 B2 describes a method to recognize the type of tissue sample to be analyzed through impedance readings inherent to the electrical properties of the tissue, which are compared to the impedance of known tissues stored in a database. Patent application Ser. No. 08/332,830 describes the use of a device to detect electrical and optical measurements to detect cervical cancer. U.S. Pat. No. 9,289,172 B2 describes a portable device that analyzes cervical tissue using electrical and optical measurements simultaneously, and that also has an auto positioning system.

In respect to the accessibility of the test, it has to be safe, hygienic, and affordable, so it can be within reach of the bottom of the pyramid. Therefore, it is fundamental that the device is able to perform the highest number of tests possible for its own amortization, in a hygienic and safe manner, and thus avoiding the outbreak of infections in healthy patients. The proposed solution is to use an affordable and functional disposable cover that allows simultaneous electrical and optical measurements to provide a diagnosis on the tissue.

U.S. Pat. No. 5,855,551 describes an Integral sheathing apparatus for tissue recognition probes that incorporates an opto-electronic section in the tip of the sheath cover for a diagnostic probe that makes both electric and optical measurements of tissue contacted by the sheath. The electrodes are an integral part of the tip section and are not an addition in the form of a separately molded section.

EP 0865761 A describes an active disposable cover able to perform electrical and optical measurements of cervical tissue, with the electrodes embedded in the plastic cover.

The main problem of the above referred disposable covers comprises that the electrodes have to embedded in the material, which makes the manufacturing process more complex and expensive. Also, the electronic components must be mounted in the sheath, which also makes the manufacturing process expensive.

In view of the above referred problem, applicant developed an active sheath in which the conductors and circuits are applied on the surface of the sheath such as in the form of a flexible circuit made of a biocompatible material and a flexible conductor or a conductive ink in the surface of the disposable cover's tip without the need to embed the electrodes or other components inside the plastic cover. Such characteristics makes the sheath of the present invention easier and quicker to manufacture at a lower cost that the sheaths of the prior art.

SUMMARY OF THE INVENTION

It is therefore a main object of the present invention to provide an active sheath for a recognition probe of a handheld cancer screening device, in which the conductors and circuits are applied on the surface of the sheath such as in the form of a flexible circuit made of a biocompatible material and a flexible conductor or a conductive ink in the surface of the disposable cover's tip without the need to embed the electrodes or other components inside the plastic cover.

It is also a main object of the present invention to provide a sheath of the above referred nature, which is easier and quicker to manufacture at a lower cost that the sheaths of the prior art.

These and other objects and advantages of the functional disposable sheath of the present invention, will become apparent to those persons having an ordinary skill in the art, from the following detailed description of the embodiments of the invention which will be made with reference to the accompanying drawings.

DETAILED DESCRIPTION OF THE INVENTION

Figure 1:
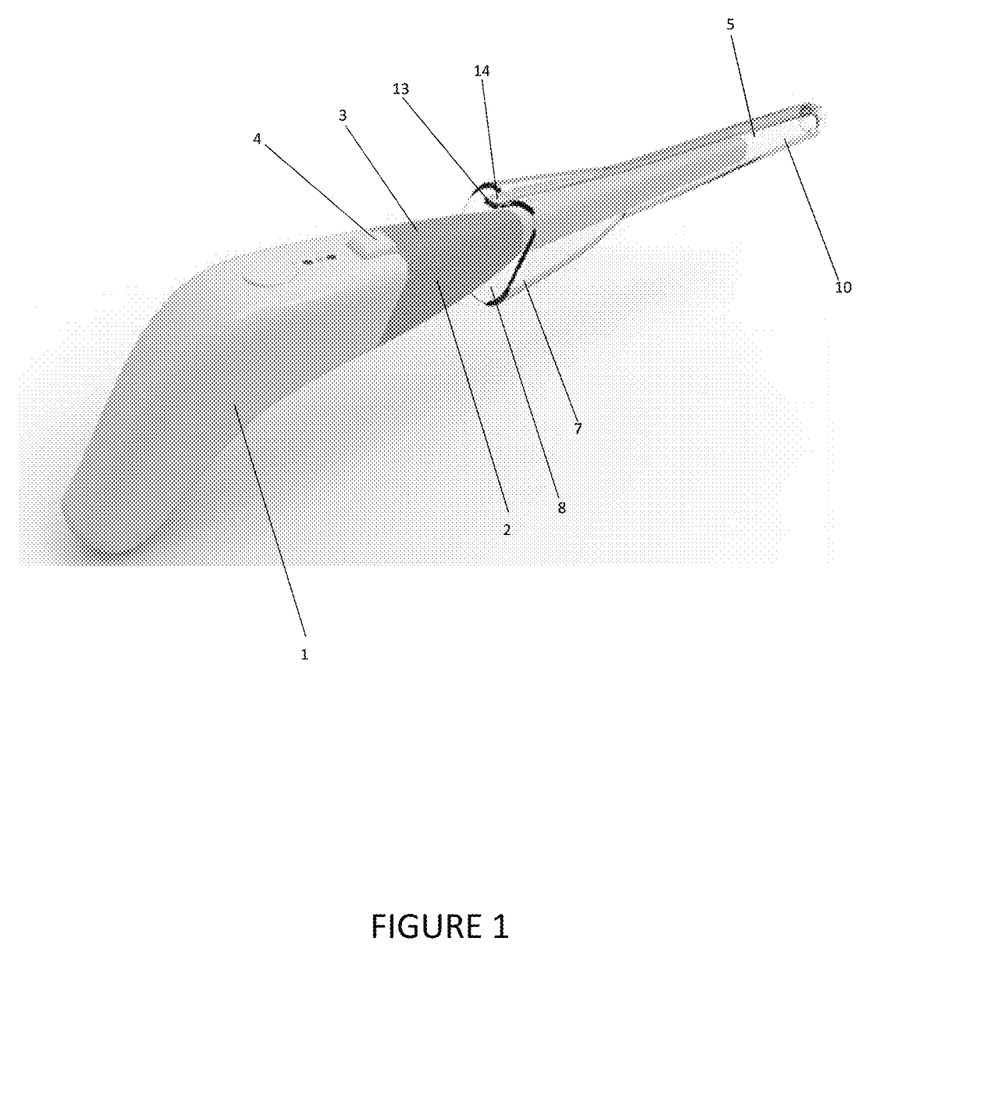
FIG. 1 is a rear side perspective view of a handheld cervical cancer screening device including a recognition probe having the disposable sheath of the present invention.

The functional disposable sheath of the present invention, for a recognition probe of a handheld cervical cancer screening device will now be described making reference to a general embodiment of a handheld cancer screening device capable of performing optical and electrical measurements on the surface of the cervix which comprises:

a hand piece (1), including all the electronic components necessary to carry out the test; and an elongated recognition probe (2) directly depending from the hand piece (1), having a quadrangular cross section and an upper surface (3);

said hand piece having a female electrical connector (4) protruding from a central portion of the upper surface (3), said female electrical connector (4) comprising a plug-in type female connector having three electrical contacts and a rectangular housing having a longitudinal axe parallel to the upper surface of the hand piece (1), wherein the plug-in type electrical connector is connected to the electronic components of the hand piece.

Figure 2:
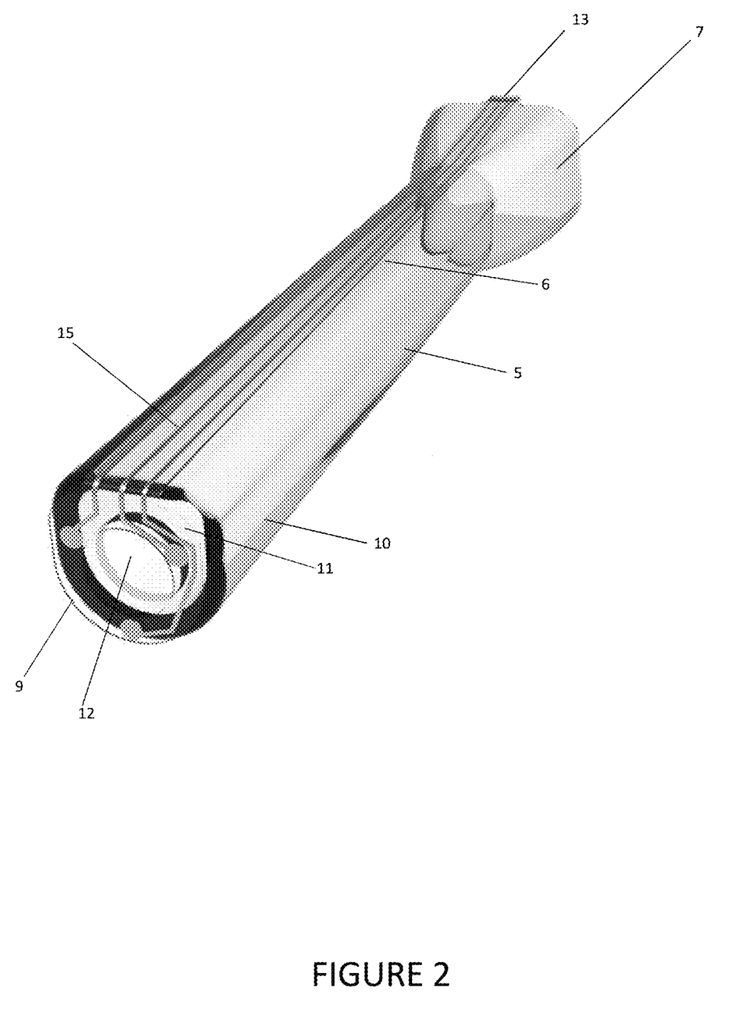
FIG. 2 is a top front perspective view of the sheath of the present invention.
Figure 3:
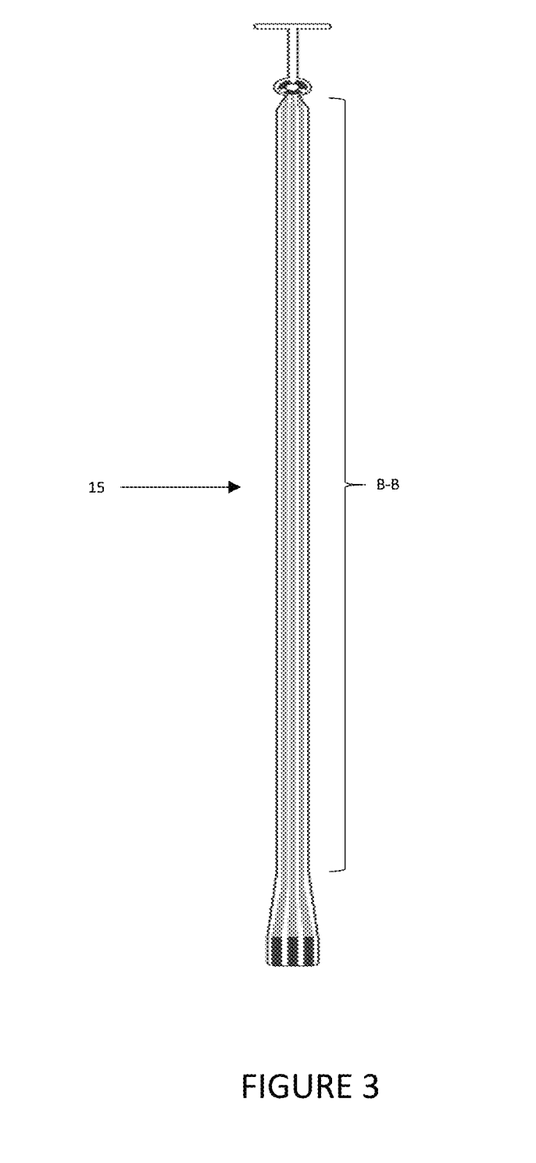
FIG. 3 is a front view of the flexible printed circuit of the sheath of the present invention.
Figure 4:
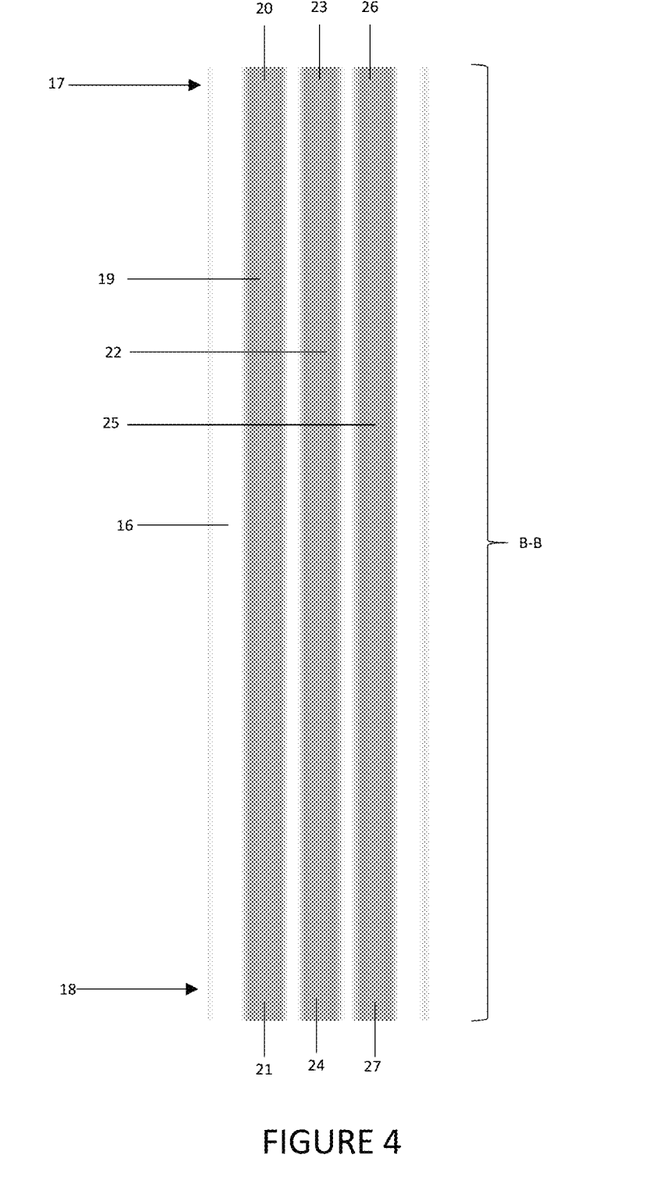
FIG. 4 is a front view of a representation of the entire main conductive section (B-B) of the flexible printed circuit of the sheath of the present invention.
Figure 5:
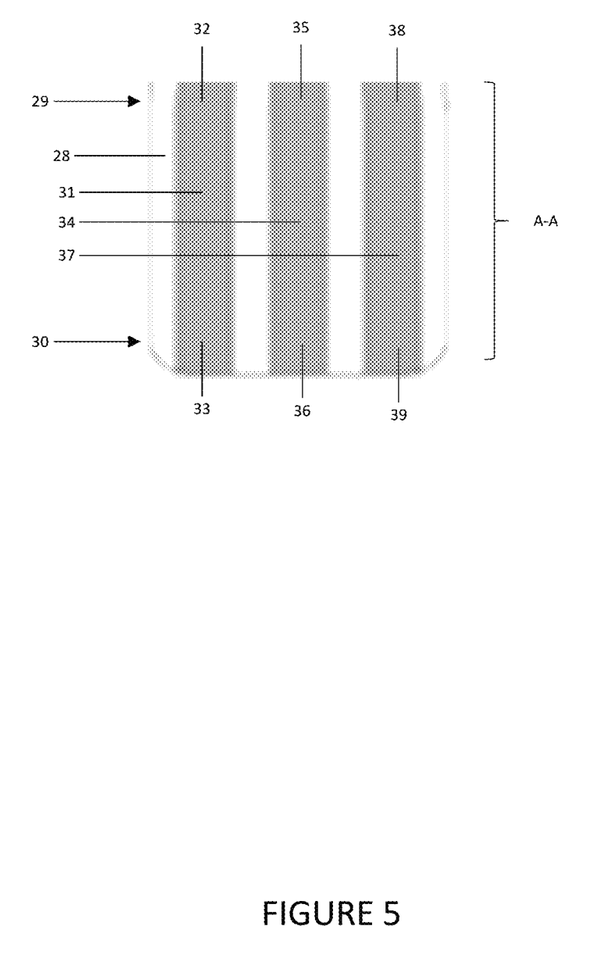
FIG. 5 is a front view of the male connection end section of the flexible printed circuit of the sheath of the present invention.
Figure 6:
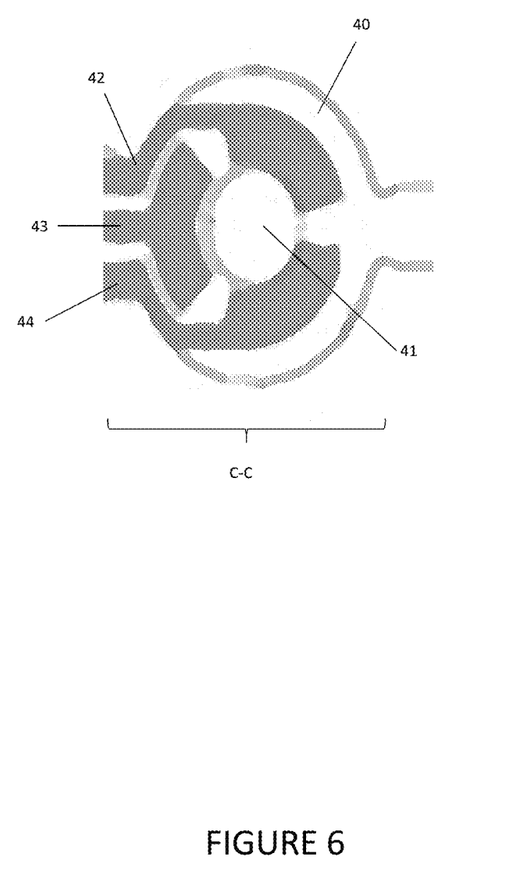
FIG. 6 is a front view of the electrode section of the flexible printed circuit of the sheath of the present invention.
Figure 7:
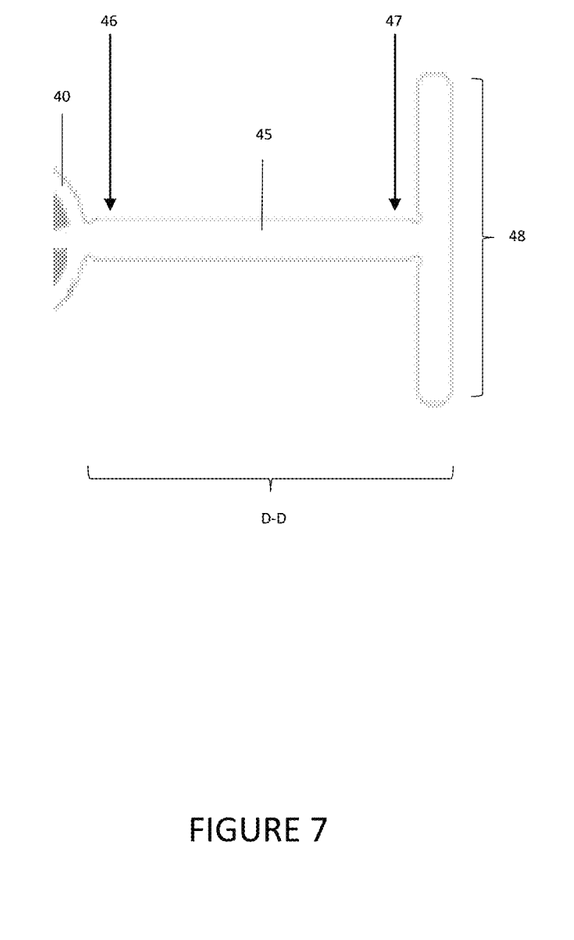
FIG. 7 is a front view of the electrode section fixing section of the flexible printed circuit of the sheath of the present invention.
Figure 8:
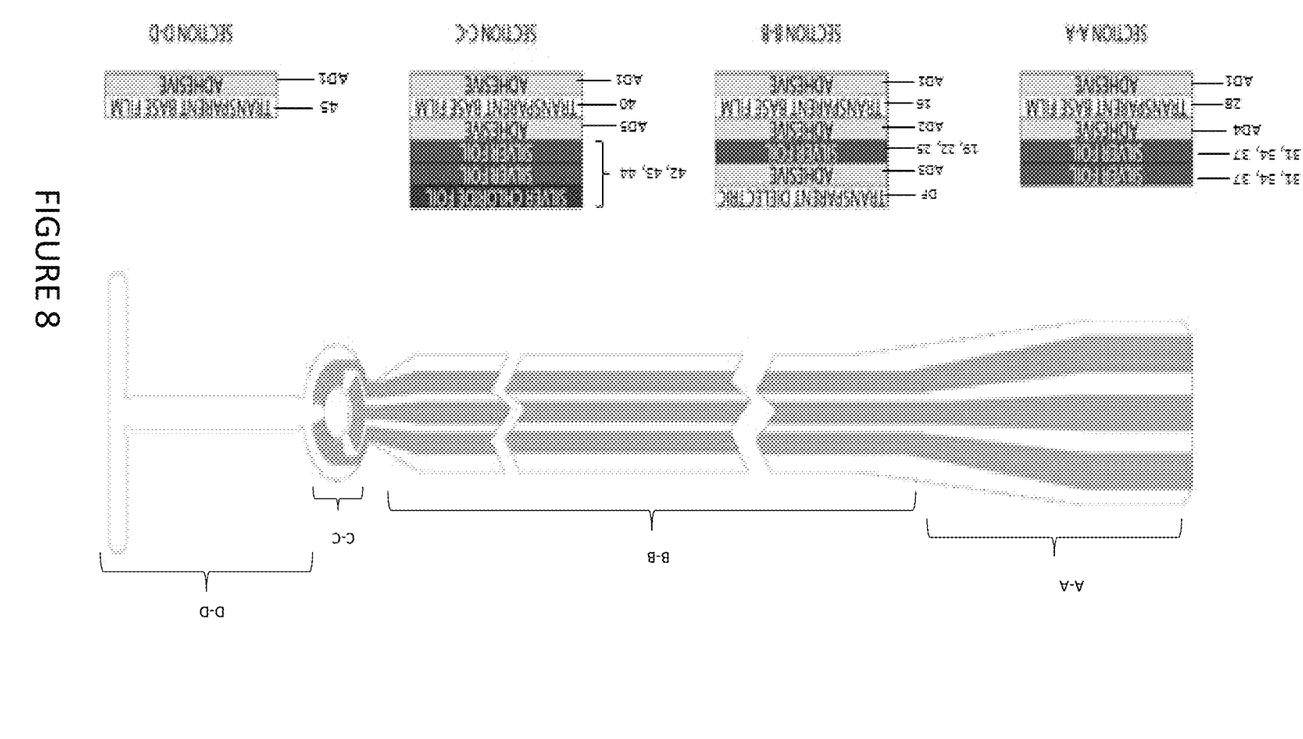
FIG. 8 is a scheme of the sections of the flexible printed circuit of the sheath of the present invention, indicating the layered components forming each section.

The functional disposable sheath of the present invention will now be described in accordance with an embodiment thereof which comprises:

An elongated sheath (5) made of a transparent polymeric material such as poly(methyl methacrylate) (PMMA) to allow carrying out optical measurements by the recognition probe (2), said sheath having: a longitudinal axe; a quadrangular cross section; an upper surface (6); a lower surface; two lateral surfaces; a first end (7) having an opening (8), a second end (9) forming a narrow end portion (10) having an oval shaped wall (11) including a central bore (12), said oval shaped wall (11) covering the tip of the sheath and being perpendicular to the longitudinal axe; said first end (7) having a quadrangular projection (13) directly depending from the upper surface (6), said quadrangular projection (13) having an upper surface (14); and wherein the opening (8) allows the entire length of the recognition probe (2) to be tightly received inside the sheath (5);

a flexible printed circuit (15) adhered to the upper surface (6) of the sheath (5), said flexible printed circuit (15) comprising:

a main conductive section (B-B) comprising the following components:

a base strip main portion (16) made of a flexible transparent plastic film having: a first end (17) and a second end (18); a first surface and a second surface;

a first layer of an adhesive substance covering all of the first surface of the base strip main portion (16);

a first flat flexible metallic conductor strip main portion (19), having a first end (20) and a second end (21), said first flat flexible metallic conductor strip main portion (19) being adhered over the first surface of the base strip main portion (16) by means of the layer of adhesive substance, and extending from the first end (17) of the base strip main portion (16) to the second end (18) of the base strip main portion (16);

a second flat flexible metallic conductor strip main portion (22), having a first end (23) and a second end (24), said second flat flexible metallic conductor strip main portion (22) being adhered over the first surface of the base strip main portion (16), next to the first flat flexible metallic conductor strip main portion (19), by means of the layer of adhesive substance, and extending from the first end (17) of the base strip main portion (16) to the second end (18) of the base strip main portion (16);

a third flat flexible metallic conductor strip main portion (25), having a first end (26) and a second end (27), said third flat flexible metallic conductor strip main portion (25) being adhered over the first surface of the base strip main portion (16), next to the second flat flexible metallic conductor strip main portion (22), by means of the layer of adhesive substance, and extending from the first end (17) of the base strip main portion (16) to the second end (18) of the base strip main portion (16);

a second layer of an adhesive substance covering all of the flat flexible metallic conductor strip main portions (19), (22), (25) and the surfaces of the base strip main portion (16) between the flat flexible metallic conductor strip main portions (19), (22), (25); and a strip of a transparent dielectric film (not shown), having: a first end and a second end; a first surface and a second surface, wherein the first surface is adhered over the three flat flexible metallic conductor strip main portions (19), (22), (25) and over the surfaces of the base strip main portion (16) between the flat flexible metallic conductor strip main portions (19), (22), (25) by means of the layer of adhesive substance, and extending from the first end (17) of the base strip main portion (16) to the second end (18) of the base strip main portion (16);

a male connection end section (A-A) comprising the following components:

a base strip connection end portion made of a flexible plastic transparent film having: a first end (29) and a second end (30); a first surface and a second surface; wherein the second end (30) depending from the first end (17) of the base strip main portion (16) of the main conductive section (B-B) and forming an integral part thereof;

a layer of an adhesive substance covering all of the first surface of the base strip connection end portion (28);

a first double layered first flat flexible metallic conductor strip connection portion (31), having a first end (32) and a second end (33), said first double layered flat flexible metallic conductor strip connection portion (31) being adhered over the first surface of the base strip connection end portion (28) by means of the layer of adhesive substance, and extending from the first end (29) of the base strip connection end portion (28) to the second end (30) thereof and the second end (30) of said first double layered flat flexible metallic conductor strip connection portion (28) depending from the first end (20) of the first flat flexible metallic conductor strip main portion (19) and forming an integral part thereof;

a second double layered flat flexible metallic conductor strip connection portion (34), having a first end (35) and a second end (36), said double layered second flat flexible metallic conductor strip connection portion (34) being adhered over the first surface of the base strip connection end portion (28), next to the first double layered flat flexible metallic conductor strip connection portion (31) by means of the layer of adhesive substance, and extending from the first end (29) of the base strip connection end portion (28) to the second end (30) thereof and the second end (36) of said second double layered flat flexible metallic conductor strip connection portion (34) depending from the first end (20) of the second flat flexible metallic conductor strip main portion (22) and forming an integral part thereof;

a third double layered third flat flexible metallic conductor strip connection portion (37), having a first end (38) and a second end (39), said third flat flexible metallic conductor strip connection portion (37) being adhered over the first surface of the base strip connection end portion (28), next to the second flat flexible metallic conductor strip connection portion (34) by means of the layer of adhesive substance, and extending from the first end (29) of the base strip connection end portion (28) to the second end (30) thereof and the second end (39) of said third flat flexible metallic conductor strip connection portion (37) depending from the first end (26) of the third flat flexible metallic conductor strip main portion (25) and forming an integral part thereof;

an electrode section (C-C) comprising the following components:

a base strip electrode portion (40) made of a flexible plastic transparent film having an oval shape including a central bore (41); a first surface and a second surface; wherein said base strip electrode portion (40) depending from the second end (18) of the base strip main portion (16) of the main conductive section (B-B) and forming an integral part thereof;

a layer of an adhesive substance covering all of the first surface of the base strip electrode portion (40);

a first electrode (42) formed by a double layer of a metallic conductor covered with a layer of silver chloride foil, said first electrode (42) being adhered over the base strip electrode portion (40) surrounding the central bore (41) by means of the layer of adhesive substance, wherein the metallic conductor of the first electrode depending from the second end (21) of the first flat flexible metallic conductor strip main portion (19) and forming an integral part thereof;

a second electrode (43) formed by a double layer of a metallic conductor covered with a layer of silver chloride foil, said second electrode (43) being adhered over the base strip electrode portion (40) surrounding the central bore (41) by means of the layer of adhesive substance, wherein the metallic conductor of the second electrode (43) depending from the second end (24) of the second flat flexible metallic conductor strip main portion (22) and forming an integral part thereof;

a third electrode (44) formed by a double layer of a metallic conductor covered with a layer of silver chloride foil, said third electrode (44) being adhered over the base strip electrode portion (40) surrounding the central bore (41) by means of the layer of adhesive substance, wherein the metallic conductor of the third electrode (44) depending from the second end (27) of the third flat flexible metallic conductor strip main portion (25) and forming an integral part thereof;

an electrode section fixing section (D-D) comprising a longitudinal strip (45) made of a flexible plastic transparent film having a first end (46) and a second end (47) and having a perpendicular strip portion (48) depending from the second end of the longitudinal strip (45) forming a general "T" shaped electrode section, the first end (46) of said longitudinal strip (45) depending from the base strip electrode portion (40) of the electrode section (C-C), forming an integral part thereof;

wherein the flexible printed circuit is longitudinally adhered to the sheath in such way that:

the second surface of the base strip main portion (16) of the main conductive section (B-B) is adhered by means of a layer of adhesive, to the upper surface (6) of the elongated sheath (5) at a longitudinally central portion in a colinear way with the quadrangular projection (13) of the sheath (5) and extending from the first end (7) to the second end (9) of the sheath (5);

the second surface of the base strip connection end portion (28) of the male connection end section (A-A) is adhered to the upper surface (14) of the quadrangular projection (13) of the sheath (5) by means of a layer of an adhesive substance;

the second surface of the base strip electrode portion (40) of the electrode section is adhered to the surface of the oval shaped wall (11) of the tip of the sheath (5) by means of a layer of an adhesive substance. Since the oval shaped wall (11) covers the tip of the sheath, the first end of the components comprising the electrode section (C-C) are bent at an angle of 90° with respect to the components comprising the main conductive section (B-B);

the longitudinal strip (45) of the electrode section fixing section (D-D) is adhered to the lower surface of the sheath (5) by means of a layer of an adhesive substance, wherein the first end (46) of said longitudinal strip (45) is bent at an angle of 90° with respect to the electrode section (C-C), and wherein the perpendicular strip portion (48) is adhered to the lower surface of the sheath (5) and to a portion of both lateral walls of the sheath (5), both perpendicularly bended at an angle of 90° with respect to the longitudinal strip (45) of the electrode section fixing section (D-D). The electrode section fixing section (D-D9 fixes the electrode section (C-C) in place, preventing it from detaching from the surface of the oval shaped wall (11), since the electrode section (C-C) is the component that is most exposed to lateral forces when the recognition probe (2) covered with the sheath (5) are introduced and retired from the vagina of a patient.

When the sheath (5) is placed on the recognition probe (2), the electrode section (C-C) together with the quadrangular projection (13), slide inside the rectangular housing of the female electrical connector (4) of the hand piece (1), in which the three double layered flat flexible metallic conductor strips connection portions (31), (34), (37) of the male connection end section of the flexible printed circuit (15) contacts the three electrical contacts of the female electrical connector (4).

Two of the electrodes of the electro de section (C-C) inject a small current to trigger the cervix cells, and one electrode measures the tissue's bioimpedance, which is conducted by the main conductive section (B-B) to the electronic components of the hand piece (1) through the connection formed by the female electrical connector (4) and the and male connection end section (A-A).

The flat flexible metallic conductor strip main portions (19), (22), (25) of the main conductive section (B-B), the double layered flat flexible metallic conductor strip connection portions (31), (34), (37) of the male connection end section (A-A), and the electrodes of the electrode section (C-C) may be comprised by a silver foil, although other materials may be used.

Since the electrodes (42), (43), (44), are the components that make direct contact with the cervix tissue, the double layer of metallic conductor and the upper layer of silver chloride of the electrodes (42), (43), (44) have the function of enhancing the electric conductivity and give more thickness to each electrode (42), (43), (44) for allowing a better contact with the cervix tissue.

The strip of transparent dielectric film of the main conductive section (B-B) electrically isolates the three flat flexible metallic conductor strip main portions (19), (22), (25) from the environment and from each other, allowing to perform electrical measurements inside the vagina without the flat flexible metallic conductor strips main portions (19), (22), (25) of the main conductive section (B-B) contacting any tissue. Thus, the electrodes (42), (43), (44) are the only components that make contact with tissue.

The sheath (5) may include an external or integrally formed longitudinal channel to facilitate the positioning of the flexible printed circuit.

Preferably, the sheath (5) and the components of the flexible printed circuit are made of biocompatible materials, however in other embodiments, at least the main conductive section of the flexible printed circuit may be drawn on the sheath with conductive paint.

Although it was described that in a preferred embodiment, the disposable sheath (5) of the present invention is adapted to a handheld cancer screening device capable of performing optical and electrical measurements on the surface of the cervix, the sheath concept may be adapted to cover the recognition probes of other kind of cancer screening device apparatuses. In this regard, and depending of each specific application, the main conductive section of the flexible printed circuit may have one or more metallic conductor strips with one or more correspondent electrodes.

Also, in such embodiments, the electrode section (C-C) may not be adhered to the tip of the sheath, since it may be adhered to an upper, lower or lateral surface of the sheath (5) for contacting portions of tissue that are not colinearly located with respect to the longitudinal axe of the sheath (5). Although not completely desirable, each section of the printed circuit may be independent from each other, independently adhered to the sheath (5) and connected to each other by any suitable means.

The sheath (5) of the present invention may be manufactured with any shape, so it can be adapted to many shapes of recognition probes Finally it must be understood that the functional disposable sheath of the present invention, is not limited exclusively to the embodiments above described and illustrated and that the persons having ordinary skill in the art can, with the teaching provided by the invention, make modifications to the functional disposable sheath of the present invention, which will clearly be within of the true inventive concept and of the scope of the invention which is claimed in the following claims.

The invention claimed is:

1. A functional disposable sheath for a cancer screening device having an electrical connection and an elongated recognition probe configured to perform optical and/or electrical measurements on the surface of a living tissue, said functional disposable sheath comprising:
    a hollow sheath made of a biocompatible material;
    a flexible conductive circuit applied to a surface of the sheath, said flexible circuit comprised of:
      an electrically isolated main section,
      an electrode section depending from the main section, and
      a connection section depending from the main section, said connection section to be electrically connected to the electrical connection of the cancer screening device,
    wherein the recognition probe of the cancer screening device has an elongated shape;
    wherein the sheath has an elongated shape made of a transparent material, said sheath having:
      a longitudinal axe,
      an upper surface,
      a lower surface,
      two lateral surfaces, and
      a first end having an opening, a second end portion having a tip portion, said tip portion forming a surface located perpendicular to the longitudinal axe,
      said first open end having a connecting projection directly depending from the upper surface, said connecting projection having an upper surface;
    wherein the opening allows the entire length of the recognition probe to be tightly received inside the sheath;
    wherein said electrically isolated main section comprises the following components:
      a base strip main portion made of a flexible plastic film, having a first end, a second end, a first surface, and a second surface,
      a first layer of adhesive substance covering all of the first surface of the base strip main portion,
      a flat flexible metallic conductor strip main portion having a first end and a second end, said flat flexible metallic conductor strip main portion being adhered over the first surface of the base strip by means of the first layer of adhesive substance, and extending from the first end of the base strip main portion to the second end of the base strip main portion,
      a second layer of adhesive substance covering the flat flexible metallic conductor strip main portion, and
      a strip of a transparent dielectric film having a first end, a second end, a first surface, and a second surface, wherein the first surface is adhered over the flat flexible metallic conductor strip main portion and over the surfaces of the base strip main portion by means of the layer of adhesive substance, and extending from the first end of the base strip main portion to the second end of the base strip main portion;
    wherein the second surface of the base strip main portion of the main conductive section is adhered by means of a layer of adhesive, to the upper surface of the elongated sheath at a longitudinally central portion in a colinear manner with the connecting projection of the sheath and extending from the first end to the second end of the sheath;
    wherein the connection section comprises the following components:
      a base strip connection end portion made of a flexible plastic transparent film having: a first end, a second end, a first surface, and a second surface, the second end depending from a first end of a corresponding base strip of the electrically isolated main section and forming an integral part thereof,
      a layer of adhesive substance covering all of the first surface of the base strip connection end portion,
      a double layered flat flexible metallic conductor strip connection portion, having a first end and a second end, said first double layered flat flexible metallic conductor strip connection portion being adhered over the first surface of the base strip connection end portion by means of the layer of adhesive substance, and extending from the first end of the base strip connection end portion to the second end thereof and the second end of said double layered flat flexible metallic conductor strip connection portion depending from a first end of a corresponding flat flexible metallic conductor strip of the electrically isolated main section and forming an integral part thereof;
    wherein the second surface of the base strip connection end portion of the male connection end section is adhered to the upper surface of the connecting projection of the sheath by means of a layer of adhesive substance;
    wherein the connection section together with the connecting projection, slide inside the housing of the female electrical connector of the cancer screening device, in which the double layered flat flexible metallic conductor strip of the male connection end section contacts the electrical contacts of the female electrical connector;

wherein said electrode section comprises the following components:

a base strip electrode portion made of a flexible plastic transparent film, and a first surface and a second surface, said base strip electrode portion depending from a second end of a correspondent main base strip of the electrically isolated main section and forming an integral part thereof, a layer of adhesive substance covering all of the first surface of the base strip electrode portion, an electrode formed by a double layer of a metallic conductor covered with a layer of silver chloride foil, said electrode being adhered over the base strip electrode portion by means of the layer of adhesive substance, wherein the metallic conductor of the electrode depending from a second end of a correspondent flat flexible metallic conductor strip of the electrically isolated main section and forming an integral part thereof; and wherein the second surface of the base strip electrode portion of the electrode section is adhered to the surface of the tip of the sheath by means of a layer of adhesive substance.

2. The functional disposable sheath as claimed in claim 1, wherein the flexible conductive circuit has silver foil conductors.

3. The functional disposable sheath as claimed in claim 1, wherein the flexible conductive circuit is adhered on the surface of the sheath.

4. The functional disposable sheath as claimed in claim 1, wherein the flexible conductive circuit is drawn on the surface of the sheath with conductive paint.

5. The functional disposable sheath as claimed in claim 1, wherein the cancer screening device has a plug-in type female connector having three electrical contacts and a rectangular housing, wherein the sheath has an elongated shape made of a transparent polymeric material, said sheath having a quadrangular cross section, and the second end forming a narrow end portion having an oval shaped wall including a central bore, said wall covering the tip of the sheath and being perpendicular to the longitudinal axe, wherein said electrically isolated main section further comprises:

a second flat flexible metallic conductor strip main portion, having a first end and a second end, said second flat flexible metallic conductor strip main portion being adhered over the first surface of the base strip, next to the first flat flexible metallic conductor strip main portion, by means of the layer of adhesive substance, and extending from the first end of the base strip main portion to the second end of the base strip main portion, and a third flat flexible metallic conductor strip main portion, having a first end and a second end, said third flat flexible metallic conductor strip main portion being adhered over the first surface of the base strip main portion, next to the second flat flexible metallic conductor strip main portion, by means of the layer of adhesive substance, and extending from the first end of the base strip main portion to the second end of the base strip main portion, the second layer of adhesive substance covering all of the flat flexible metallic conductor strip main portions and the surfaces of the base strip main portion between the flat flexible metallic conductor strip main portions, and the first surface of the strip of transparent dielectric film is adhered over the three flat flexible metallic conductor strip main portions and over the surfaces of the base strip main portion between the flat flexible metallic conductor strip main portions by means of the layer of adhesive substance, and extending from the first end of the base strip main portion to the second end of the base strip main portion.

6. The functional disposable sheath as claimed in claim 1, wherein the cancer screening device has a plug-in type female connector having three electrical contacts and a rectangular housing, wherein the sheath has an elongated shape made of a transparent polymeric material, said sheath having a quadrangular cross section, and the second end forming a narrow end portion having an oval shaped wall including a central bore, said wall covering the tip of the sheath and being perpendicular to the longitudinal axe, wherein said connection section further comprises the following components:

a second double layered flat flexible metallic conductor strip connection portion, having a first end and a second end, said second double layered flat flexible metallic conductor strip connection portion being adhered over the first surface of the base strip connection end portion, next to the double layered first flat flexible metallic conductor strip connection portion by means of the layer of adhesive substance, and extending from the first end of the base strip connection end portion to the second end thereof and the second end of said second double layered flat flexible metallic conductor strip connection portion depending from a correspondent first end of a corresponding second flat flexible metallic conductor of the electrically isolated main section and forming an integral part thereof, and a third double layered flat flexible metallic conductor strip connection portion, having a first end and a second end, said third double layered flat flexible metallic conductor strip connection portion being adhered over the first surface of the base strip connection end portion, next to the second double layered flat flexible metallic conductor strip connection portion by means of the layer of adhesive substance, and extending from the first end of the base strip connection end portion to the second end thereof and the second end of said third double layered flat flexible metallic conductor strip connection portion depending from the first end of a corresponding third flat flexible metallic conductor of the electrically isolated main section and forming an integral part thereof.

7. The functional disposable sheath as claimed in claim 1, wherein the cancer screening device has a plug-in type female connector having three electrical contacts and a rectangular housing, wherein the sheath has an elongated shape made of a transparent polymeric material, said sheath having a quadrangular cross section, and the second end forming a narrow end portion having an oval shaped wall including a central bore, said wall covering the tip of the sheath and being perpendicular to the longitudinal axe, wherein the base strip electrode portion has an oval shape including a central bore, wherein said electrode section further comprises the following components:
- a second electrode formed by a double layer of a metallic conductor covered with a layer of silver chloride foil, said second electrode being adhered over the base strip electrode portion surrounding the central bore by means of the layer of adhesive substance, wherein the metallic conductor of the second electrode depending from the second end of a correspondent second flat flexible metallic conductor strip of the electrically isolated main section and forming an integral part thereof, and
- a third electrode formed by a double layer of a metallic conductor covered with a layer of silver chloride foil, said third electrode being adhered over the base strip electrode portion surrounding the central bore by means of the layer of adhesive substance, wherein the metallic conductor of the third electrode depending from the second end of a correspondent third flat flexible metallic conductor strip of the electrically isolated main section and forming an integral part thereof, and wherein the second surface of the base strip electrode portion of the electrode section is adhered to the surface of the oval shaped wall of the tip of the sheath at an angle of 90° with respect to the electrically isolated main section, by means of the layer of adhesive substance.

8. The functional disposable sheath as claimed in claim 7, further comprising:
- an electrode section fixing section comprising a longitudinal strip made of a flexible plastic transparent film having a first end and a second end and having a perpendicular strip portion depending from the second end of the longitudinal strip forming a general "T" shaped electrode section, the first end of said longitudinal strip depending from the base strip electrode section of the electrode section, forming an integral part thereof,
- wherein the longitudinal strip of the electrode section fixing section is adhered to the lower surface of the sheath by means of a layer of adhesive substance, wherein the first end of said longitudinal strip is bent at an angle of 90° with respect to the electrode section, and
- wherein the perpendicular strip portion is adhered to the lower surface and to a portion of both lateral walls of the sheath, both perpendicularly bended at an angle of 90° with respect to the longitudinal strip of the electrode section fixing section.

\* \* \* \* \*